United States Patent
Jun et al.

(10) Patent No.: US 6,353,139 B1
(45) Date of Patent: Mar. 5, 2002

(54) METHOD FOR PREPARING KETONES

(75) Inventors: Chul Ho Jun, 103-12-3, Doklipmoon Samho Apt., Youngchon-dong 100, Seodaemoon-ku, Seoul; Dae Yon Lee, Kyunggi-do; Hyuk Lee, Seoul; Jun Bae Hong, Kyunggi-do, all of (KR)

(73) Assignee: Chul Ho Jun, Seoul (KR)

( * ) Notice: Subject to any disclaimer, the term of this patent is extended or adjusted under 35 U.S.C. 154(b) by 0 days.

(21) Appl. No.: 09/792,240

(22) Filed: Feb. 26, 2001

(51) Int. Cl.$^7$ .................................................. C07C 45/69
(52) U.S. Cl. ........................ 568/317; 568/312; 568/314; 568/349; 568/395
(58) Field of Search ................................ 568/312, 314, 568/317, 349, 395

(56) References Cited

U.S. PATENT DOCUMENTS 4,241,206 A * 12/1980 Suggs ........................ 542/424

OTHER PUBLICATIONS

Chelation–assisted intermolecular hydroacylation: direct synthesis of ketone from aldehyde and 1–alkene; Jun et al, J.Org.Chem., 62, pp 1200–1201 (1997).*

Activation of aldehyde C–H bonds to oxidative addition via formation of 3–methyl–2-aminopyridyl aldimines and related compounds: rhodium based catalytic hydroacylation; Suggs, J.Am.Chem.Soc., 101(2), p.489 (1979).*

* cited by examiner

*Primary Examiner*—Sreeni Padmanabhan
(74) *Attorney, Agent, or Firm*—Harrison & Egbert

(57) ABSTRACT

A method for preparing ketones has advantages of improving yields and reducing the time of the reactions due to high efficiency of catalysts. Ketones are prepared by reacting an aliphatic or an aromatic aldehyde with a vinyl olefin having an aliphatic or aromatic alkyl moiety in the presence of a transition metal catalyst, 2-aminopyridine catalyst, a primary amine and an acid, as catalysts and additives.

3 Claims, No Drawings

METHOD FOR PREPARING KETONES

BACKGROUND OF THE INVENTION

1. Field of the Invention

The present invention relates, in general, to a method for preparing a ketone and, more particularly, to a method for preparing a ketone by use of aldehyde and olefins as starting materials in the presence of a transition metal catalyst.

2. Description of Related Art

Until recently, the introduction of carbonyl, one of the most important organic groups, into organic compounds has been in extensive study for preparing ketones. In one of the most typical methods, aldehyde is reacted with a nucleophilic organic metal compound, such as alkylmagnesium halide, to give secondary alcohol which is then oxidized into ketone with the aid of various oxidizers. However, this method suffers from several disadvantages: it must pass through many reaction steps and produces many unnecessary by-products during the reaction steps.

In an effort to avoid these problems, active research has been directed to hydroacylation techniques of preparing ketones directly from olefins and aldehyde by use of metal catalysts. Conventional hydroacylation techniques have the disadvantage of easily causing side-reactions, such as a formation of alkane from aldehyde through decarbonylation. So, in order to suppress such decarbonylation, a technique for introducing carbon monoxide or ethylene gas under high pressure is known, but has disadvantages of using gas of high pressure and vigorous reaction conditions. Alternatively, a hydroacylation technique for synthesizing ketones from benzaldehyde and vinyl silane at room temperature by use of a cobalt catalyst is reported, however, this technique is disadvantageous in terms of low feasibility, because usable olefins are defined in vinyl silane or its derivatives. A recent hydroacylation technique, capable of being conducted under relatively simple and mild conditions, synthesizes ketones by introducing a transition metal catalyst and 2-aminopyridine derivatives as additives, in addition to aldehyde and olefin, as illustrated in the following chemical reaction formula 1.

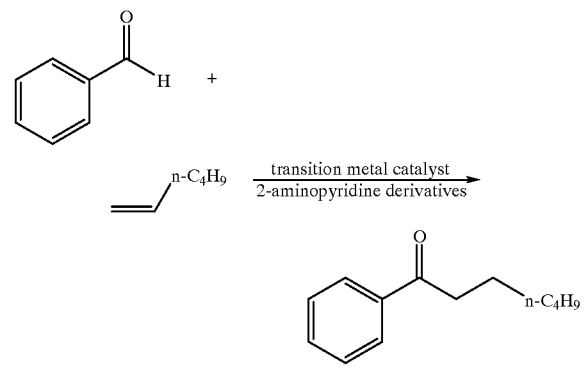

The above reaction is specifically shown in chemical reaction formula 2, below.

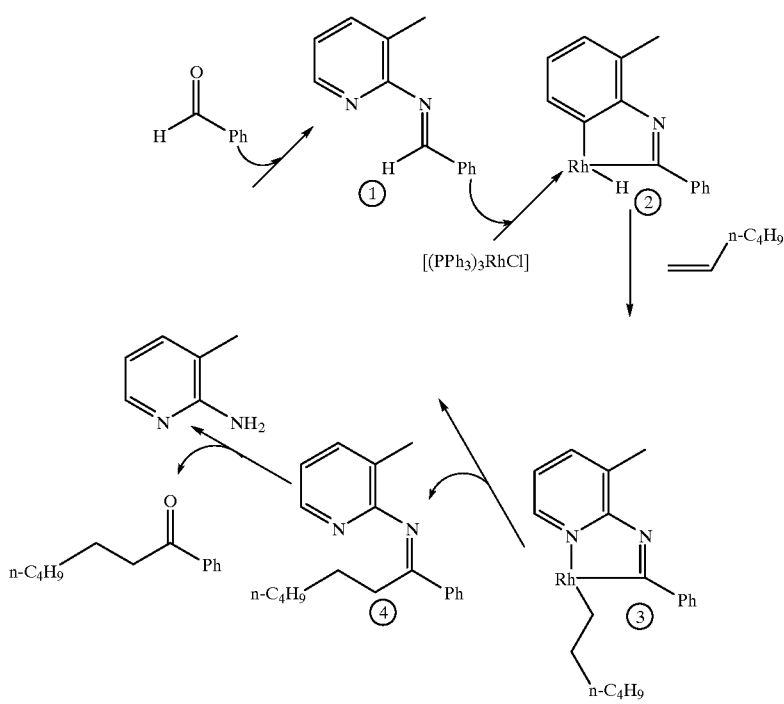

As illustrated in said reaction formula, aldimine 1 resulting from a reaction of aldehyde with a 2-aminopyridine derivative, is reacted with a metal catalyst to form a metal hydride 2, which is then reacted with olefin to afford ketimine with the aid of an alkyl metal compound 3. Then, ketimine 4 is hydrolyzed with water to produce ketone.

Though conducted under simple and mild conditions, this method suffers from the disadvantages of using 10 mol % metal catalysts and 20 mol % 2-aminopyridine derivatives as catalysts useful in the reaction, and heating the reactants for 60 hours or more in order to obtain ketone with high yields of 80% or higher.

BRIEF SUMMARY OF THE INVENTION

Leading to the present invention, thorough and intensive research on the synthesis of ketones, repeated by the present invention aiming to efficiently improve a reaction by use of a 2-aminopyridine derivative and a transition metal catalyst among the preparation of ketones through a reaction of aldehyde with olefins (hydroacylation), resulted in the finding that addition of acids and primary amines can increase efficiency of the catalyst not only to improve the yields of ketones but also to reduce the time of the reaction.

Therefore, it is an object of the present invention to overcome the above problems encountered in the prior art and to provide a method for preparing a ketone with high yields.

DETAILED DESCRIPTION OF THE INVENTION

The present invention is directed to the synthesis of ketones by reacting aldehyde with olefins in the presence of catalysts and additives. A transition metal catalyst, a 2-aminopyridine derivative, amines and acids, useful as catalysts and additives, are reacted together to prepare ketones, as illustrated in the following chemical reaction formula 3:

Useful as starting materials in the present invention are aldehyde and olefins. As aldehyde, all aldehydes such as an aromatic or aliphatic aldehyde can be used, and as olefins, use can be made of not only ethylene but also almost all vinyl-containing olefins having an aliphatic or aromatic alkyl moiety. Examples of transition metal catalysts suitable for the preparation of ketones include Wilkins catalysts such as $(PPh_3)_3RhCl$, rhodium monovalent catalysts such as $[Rh(C_8H_{14})_2Cl]_2$, and rhodium trivalent catalyst such as $[RhCl_3AH_2O]$. When rhodium monovalent or trivalent catalyst is employed, various phosphine compounds, such as triphenyl phosphine ($PPh_3$), are preferably added together. Transition metal compounds, such as ruthenium or iridium, may be used as catalysts, but have inferior reactivity to rhodium compounds.

In combination with the transition metal catalyst, a 2-aminopyridine derivative is used according to the present invention. A variety of 2-aminopyridine derivatives may be used as additional catalysts. In primary amines, most aromatic and aliphatic amines, including aniline, benzylamine, cyclohexylamine, and tert-butylamine, may be used. As for acids, various aromatic and aliphatic acids include, but are not limited to, benzoic acid, acetic acid, and p-toluene sulfonic acid.

A suitable organic solvent, if not indispensable for the synthesis, is helpful in increasing the efficiency of the catalysts or additives.

In the synthesis of ketones according to the present invention, the reactants are reacted in the reaction mechanism shown in the following chemical reaction formula 4:

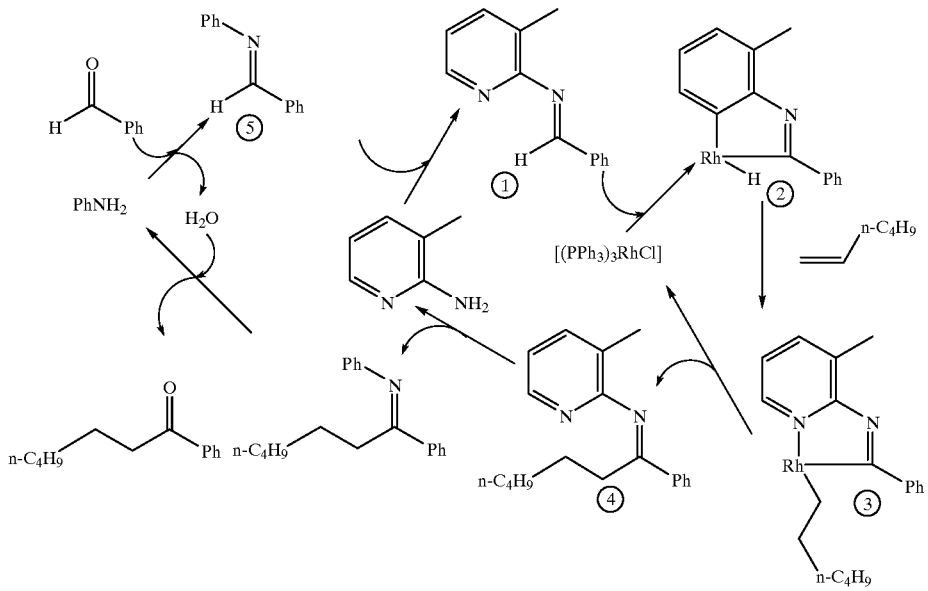

As shown in the above chemical reaction formula, the reaction starts with the formation of aldimine 5 through the condensation of aldehyde with aniline. Then, a different aldimine 1 is formed through a transimination of aldimine 5 with 2-amino-3-picoline, followed by reacting with a transition metal catalyst to afford a metal hydride 2, which is then reacted with 1-hexene with the aid of alkyl metal compound 3 to produce ketimine 4. This ketimine is hydrolyzed by water to form ketone, or reacted with aniline through transimination to form a different ketimine which is then hydrolyzed by water to produce ketones. Aniline plays a role in easing production of aldimine 1 through combination of 2-amino-3-picoline with aldehyde, an important intermediate of reaction substrates. A formation of aldimine 1 through a reaction of transimination from aldimine 5 resulting from aniline and aldehyde is faster than a direct formation of aldimine 1 from aldehyde and 2-amino-3-picoline. Acids useful as the additives are responsible for easily carrying out the condensation or transimination. Therefore, the hydroacylation using two such additives, namely aniline and acids, in the present invention has a much higher reaction efficiency and faster reaction time than hydroacylation by use of known Rh(I) compounds and 2-amino-3-picoline.

A better understanding of the present invention may be obtained in light of the following examples which are set forth to illustrate, but are not to be construed to limit the present invention.

EXAMPLE 1

In a 500 ml pressure reactor, benzaldehyde 53 mg (0.5 mmol), 2-amino-3-picoline 11 mg (0.1 mmol), benzoic acid 4 mg (0.03 mmol), aniline 28 mg (0.3 mmol) and 1-hexene 210 mg 2.5 mmol) were placed and dissolved in toluene 80 mg (0.87 mmol). The mixture was stirred at normal temperature for 2–3 minutes, and then combined with Rh(PPh$_3$)$_3$Cl 9.25 mg (0.01 mmol). While the reactor was stopped with a stopper, the reactants were heated at 130° C. for 1 hour with stirring. After completion of the reaction, heptanophenone (93 mg, 0.49 mmol) was found to be obtained at a yield of 98 % as measured by column chromatography.

Under the same condition, a variety of olefins were employed. The results are given in Table 1, below.

TABLE

| Nos. | Olefins | Products | Yield (%) |
|---|---|---|---|
| 1 | 1-Pentene | 1-Phenyl-1-Hexanone | 83 |
| 2 | 1-Hexene | 1-Phenyl-1-Heptanone | 98 |
| 3 | 1-Octene | 1-Phenyl-1-Nonanone | 99 |
| 4 | 3,3-Dimethyl-1-Butene | 4.4-Dimethyl-1-Phenyl-1-Pentanone | 84 |
| 5 | Arylphenyl Ether | 4-Phenoxy-1-Phenyl-1-Propanone | 95 |
| 6 | 2,3,4,5,6-Pentafluorostyrene | 3-Pentafluorophenyl-Propiophenone | 98 |
| 7 | Norbornene | Bicyclo[2.2.1]hep-2-yl-phenyl-methanone | 47 |
| 8 | Trimethyl-Vinyl-Silane | 1-phenyl-3-trimethylsilanyl-propan-1-one | 95 |

EXAMPLE 2

Under the same reaction procedure and conditions as in Example 1 (2-amino-3-picoline 0.1 mmol, bezoic acid 0.03 mmol, aniline 0.3 mmol, 1-hexene 2.5 mmol, toluene 0.87 mmol), various kinds of aldehyde 0.5 mmol were introduced in each 500 ml pressure reactor. The mixture was stirred at normal temperature for 2–3 minutes, and then combined with Rh(PPh$_3$)$_3$Cl 9.25 mg (0.01 mmol). While the reactor was stopped with a stopper, the reactants were heated at 130° C. for 1 hour with stirring. After completion of the reaction, column chromatography was conducted to determine the yields of products according to various aldehydes and the results are given in Table 2, below.

TABLE 2

| Nos. | Aldehyde | Products | Yield (%) |
|---|---|---|---|
| 1 | Benzaldehyde | Heptanophenone | 98 |
| 2 | Biphenyl-4-cabaaldehyde | 1-biphenyl-4-yl-heptan-1-one | 95 |
| 3 | Naphthalene-2-cabaaldehyde | 1-naphthalen-2-yl-heptan-1-one | 91 |
| 4 | 4-methoxy-benzaldehyde | 1-(4-methoxy-phenyl)-heptane-1-one | 79 |
| 5 | 4-dimethylamino-benzaldehyde | 1-(4-dimethylamino-phenyl)-heptan-1-one | 57 |
| 6 | 4-methyl-benzaldehyde | 1-p-toryl-heptane-1-one | 88 |
| 7 | 4-bromo-benzaldehyde | 1-(4-bromophenyl)-heptane-1-one | 47 |
| 8 | 4-trifluoromethyl-benzaldehyde | 1-(4-trifluoromethyl-phenyl)-heptan-1-one | 71 |
| 9 | 4-fluoro-benzaldehyde | 1-(4-fluorophenyl)-heptan-1-one | 88 |
| 10 | 3-phenyl-propionaldehyde | 1-phenyl-octan-3-one | 71 |

EXAMPLE 3

Under the same reaction procedure and conditions as in Example 1 (benzaldehyde 0.5 mmol, aniline 0.3 mmol, bezoic acid 0.03 mmol, 1-hexene 2.5 mmol, toluene 0.87 mmol), various 2-aminopyridine derivatives 0.1 mmol as shown in the following table 3, were added to each 500 ml pressure reactor. The mixture was stirred at normal temperature for 2–3 minutes and then combined with Rh(PPh$_3$)$_3$Cl 0.01 mmol. While the reactor was stopped with a stopper, the reactants were heated at 130° C. for 1 hour with stirring. After completion of the reaction, gas chromatography was conducted to determine the yields of heptanophenone, products from various aminopyridine derivatives. The results are presented in Table 3, below.

TABLE 3

| Nos. | 2-aminopyridine derivatives | Yield (%) |
|---|---|---|
| 1 | 2-aminopyridine | 18 |
| 2 | 2-amino-3-picoline | 100 |
| 3 | 2-amino-4-picoline | 11 |
| 4 | 2-amino-5-picoline | 12 |
| 5 | 2-amino-6-picoline | 3 |

EXAMPLE 4

Under the same reaction procedure and conditions as in Example 1 (benzaldehyde 0.5 mmol, 2-amino-3-picoline 0.1 mmol, aniline 0.3 mmol, 1-hexene 2.5 mmol, toluene 0.87 mmol), various kinds of acids 0.03 mmol as shown in the following table 4, were added to each 500 ml pressure reactor. The mixture was stirred at normal temperature for 2–3 minutes and then combined with Rh(PPh$_3$)$_3$Cl 0.01 mmol. While the reactor was stopped with a stopper, the reactants were heated at 130° C. for 1 hour with stirring. After completion of the reaction, gas chromatography was conducted to determine the yields of heptanophenone, products from various acids and the results are given in Table 4, below.

TABLE 4

| Nos. | Acid | Yield (%) |
|---|---|---|
| 1 | Octanoic acid | 69 |
| 2 | Acetic acid | 73 |
| 3 | 4-methyl-benzoic acid | 82 |
| 4 | Benzoic acid | 100 |

TABLE 4-continued

| Nos. | Acid | Yield (%) |
|---|---|---|
| 5 | 4-fluoro-benzoic acid | 100 |
| 6 | 4-chloro-benzoic acid | 100 |
| 7 | Chloro-acetic acid | 95 |
| 8 | p-toluene sulfonic acid | 43 |
| 9 | Trifluoroacetic acid | 35 |

EXAMPLE 5

Under the same reaction procedure and conditions as in Example 1 (benzaldehyde 0.5 mmol, 2-amino-3-picoline 0.1 mmol, bezoic acid 0.03 mmol, 1-hexene 2.5 mmol, toluene 0.87 mmol), various kinds of amines 0.3 mmol as shown in the following table 5, were added to each 500 ml pressure reactor. The mixture was stirred at normal temperature for 2–3 minutes and then combined with $Rh(PPh_3)_3Cl$ 0.01 mmol. While the reactor was stopped with a stopper, the reactants were heated at 130° C. for 1 hour with stirring. After completion of the reaction, column chromatography was conducted to determine the yields of heptanophenone, products according to various amines. The results are given in Table 5, below.

TABLE 5

| Nos. | Amine | Yield (%) |
|---|---|---|
| 1 | No | 33 |
| 2 | Aniline | 39 |
| 3 | Benzylamine | 87 |
| 4 | Cyclohexylamine | 79 |
| 5 | tert-butylamine | 59 |

EXAMPLE 6

Under the same reaction procedure and conditions as in Example 1 (benzaldehyde 0.5 mmol, 2-amino-3-picoline 0.1 mmol, aniline 0.3 mmol, bezoic acid 0.03 mmol, 1-hexene 2.5 mmol, toluene 0.87 mmol), the mixture in a 500 ml pressure reactor was stirred at normal temperature for 2–3 minutes and then various transition metal catalysts as shown in the following table 6 were added to each reactor. While the reactor was stopped with a stopper, the reactants were heated at 130° C. for 1 hour with stirring. After completion of the reaction, gas chromatography was conducted to determine the yields of heptanophenone, products according to various transition metal catalysts. The results are shown in Table 6, below.

TABLE 6

| Nos. | Transition metal catalyst | Yield (%) |
|---|---|---|
| 1 | $Rh(PPh_3)_3Cl$ | 100 |
| 2 | $RhCl_3$ + $PPh_3$ (3 equiv.) | 76 |
| 3 | $[Rh(C_8H_{14})_2Cl]_2$ + $PPh_3$ (2.5 equiv.) | 100 |
| 4 | $Rh(Co)Cl(PPh_3)_2$ | 5 |
| 5 | $[r(PPh_3)_3Cl$ | 4 |
| 6 | $Ru_3(Co)_{12}$ | 3 |
| 7 | $Ru(PPh_3)_3Cl_2$ | 1 |

EXAMPLE 7

Under the same reaction procedure and conditions as in Example 1 (benzaldehyde 0.5 mmol, 2-amino-3-picoline 0.1 mmol, aniline 0.3 mmol, bezoic acid 0.03 mmol, 1-hexene 2.5 mmol, toluene 0.87 mmol), the mixture in a 500 ml pressure reactor was stirred at normal temperature for 2–3 minutes and then $[Rh(C_8H_{14})_2Cl]_2$ 0.01 mmol and various phosphine ligands 0.025 mmol as shown in the following table 7 were introduced into each reactor. While the reactor was stopped with a stopper, the reactants were heated at 130° C. for 1 hour with stirring. After completion of the reaction, gas chromatography was conducted to determine the yields of heptanophenone, products from various phosphine ligands. The results are given in Table 7, below.

TABLE 7

| Nos. | Phosphine Ligand | Amount (equiv.) | Yield (%) |
|---|---|---|---|
| 1 | $PPh_3$ (30 min) | 2.0 | 74 |
| 2 | $PPh_3$ (30 min) | 2.5 | 82 |
| 3 | $PPh_3$ (30 min) | 3.0 | 75 |
| 4 | $PPh_3$ (60 min or lower) | 2.5 | 100 |
| 5 | $P(p-MeC_6H_4)_3$ | 2.5 | 99 |
| 6 | $P(p-MeOC_6H_4)_3$ | 2.5 | 99 |
| 7 | $P(o-MeC_6H_4)_3$ | 2.5 | 15 |
| 8 | $PCy_3$ | 2.5 | 25 |
| 9 | $PPhCy_2$ | 2.5 | 12 |
| 10 | $PBu_3$ | 2.5 | 10 |
| 11 | DPPE | 2.5 | 2 |

EXAMPLE 8

Under the same reaction procedure and conditions as in Example 1 (benzaldehyde 0.5 mmol, 2-amino-3-picoline 0.1 mmol, aniline 0.3 mmol, bezoic acid 0.03 mmol), 1-hexene and toluene at various amounts as shown in the following table 8, were added to each 500 ml pressure reactor. The mixture was stirred at normal temperature for 2–3 minutes and then combined with $Rh(PPh_3)_3Cl$ 0.01 mmol. While the reactor was stopped with a stopper, the reactants were heated at 130 ° C. for 1 hour with stirring. After completion of the reaction, gas chromatography was conducted to determine the yields of heptanophenone, products according to 1-hexene and toluene of various amounts. The results are given in Table 8, below.

TABLE 8

| Nos. | Amount of 1-Hexene (mmol) | Amount of Toluene (mmol) | Yield (%) |
|---|---|---|---|
| 1 | 1.0 | 0.87 | 42 |
| 2 | 1.5 | 0.87 | 66 |
| 3 | 2.0 | 0.87 | 93 |
| 4 | 2.5 | 0.87 | 100 |
| 5 | 2.5 | 0 | 100 |

EXAMPLE 9

Under the same reaction procedure and conditions as in Example 1 (benzaldehyde 0.5 mmol, 2-amino-3-picoline 0.1 mmol, aniline 0.3 mmol, bezoic acid 0.03 mmol, 1-hexene 2.5 mmol, toluene 0.87 mmol), the mixture in a 500 ml pressure reactor was stirred at normal temperature for 2–3 minutes and then combined with $Rh(PPh_3)_3Cl$ 0.01 mmol. While the reactor was stopped with a stopper, the reactants were stirred at 130 ° C. for various reaction times as shown in the following table 9. After completion of the reaction, gas chromatography was conducted to determine the yields of heptanophenone, products according to various period of times and the results are given in Table 9, below.

TABLE 9

| Nos. | Time (min) | Yield (%) |
|---|---|---|
| 1 | 15 | 52 |
| 2 | 30 | 74 |
| 3 | 45 | 89 |
| 4 | 60 | 100 |
| 5 | 120 | 100 |

EXAMPLE 10

Under the same reaction procedure and conditions as in Example 1 (benzaldehyde 0.5 mmol, 2-amino-3-picoline 0.1mmol, aniline 0.3 mmol, bezoic acid 0.03 mmol, 1-hexene 2.5 mmol, toluene 0.87 mmol), the mixture in a 500 ml pressure reactor was stirred at normal temperature for 2–3 minutes and then combined with Rh(PPh$_3$)$_3$Cl 1 0.01 mmol. While the reactor was stopped with a stopper, the reactants were stirred at various temperatures (70–130° C.) as shown in the following table 10 for 1 hour. After completion of the reaction, gas chromatography was conducted to determine the yields of heptanophenone, products according to various temperatures and the results are given in Table 10, below.

TABLE 10

| Nos. | Temp. (° C.) | Yield (%) |
|---|---|---|
| 1 | 70 | 13 |
| 2 | 100 | 52 |
| 3 | 130 | 100 |
| 4 | 150 | 100 |
| 5 | 170 | 100 |
| 6 | 130 (30 min) | 74 |
| 7 | 150 (30 min) | 82 |
| 8 | 170 (30 min) | 86 |

EXAMPLE 11

In order to compare the yields of ketones prepared according the inventive hydroacylation using not only transition compounds and 2-aminopyridine derivatives but also primary amines and acids as additives and conventional hydroacylation using transition compounds and 2-aminopyridine derivatives, heptanophenones of the present invention were obtained in the same manner as in Example 1, except that the time of the reaction was changed as shown in Table 11. Their yields were measured. In addition, heptanophenones according to conventional hydroacylation were obtained in the same manner as in Example 1, except that aniline and bezoic acid, among reaction catalysts, were not used and the time of the reaction were changed as shown in Table 11. Their yields were measured and the results are presented in Table 11, below.

TABLE 11

| Nos. | Time (h) | Conventional Hydroacylation | Inventive Hydroacylation |
|---|---|---|---|
| 1 | 0.5 | 8 | 62 |
| 2 | 1 | 9 | 100 |
| 3 | 2 | 12 | 100 |
| 4 | 4 | 16 | 100 |
| 5 | 6 | 19 | 100 |
| 6 | 8 | 20 | 100 |
| 7 | 12 | 24 | 100 |

As described above, in the method of the present invention, the efficiency of the catalysts are drastically increased to improve yields of ketones and to reduce the time of the reaction. Also, the present invention is very advantageous in that it can be applied to all of aldehydes and olefins as reaction substrates, capable of being used in preparation of ketones.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A method for preparing a ketone, comprising reacting an aliphatic or aromatic aldehyde with an aliphatic or aromatic alkyl moiety-containing vinyl olefin as starting materials in the presence of a transition metal catalyst, a 2-aminopyridine derivative, a primary amine and an acid, as catalysts and additives.

2. The method as set forth in claim 1, wherein the transition metal catalyst is selected from the group consisting of rhodium monovalent compounds, phosphine-added rhodium monovalent compounds, rhodium trivalent compounds, phosphine-added rhodium trivalent compounds, ruthenium compounds, iridium compounds or mixtures thereof.

3. A method for preparing a ketone, comprising the steps of:

producing a different aldimine as a reaction intermediate through transimination of 2-aminopyridine derivatives with aldimine resulting from the condensation of aldehyde with amines;

coordinating a transition metal catalyst to the pyridine radical of the aldimine to cleave a carbon-hydrogen bond of the reactant aldehyde;

coordinating a reactant olefin to the metal of the transition metal catalyst to produce ketimine; and hydrolyzing the ketimine with the water resulting from the condensation to recover the amine.

* * * * *